(12) United States Patent
Liao

(10) Patent No.: US 7,071,279 B2
(45) Date of Patent: *Jul. 4, 2006

(54) HIGH REFRACTIVE INDEX AND OPTICALLY CLEAR COPOLY (CARBOSILANE AND SILOXANE) ELASTOMERS

(75) Inventor: Xiugao Liao, Irvine, CA (US)

(73) Assignee: STAAR Surgical Company, Monrovia, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/826,498

(22) Filed: Apr. 16, 2004

(65) Prior Publication Data

US 2004/0198865 A1   Oct. 7, 2004

Related U.S. Application Data

(62) Division of application No. 10/308,803, filed on Dec. 3, 2002.

(51) Int. Cl.
C08G 77/12 (2006.01)

(52) U.S. Cl. .................. 528/31; 528/32; 524/91; 524/359; 524/588

(58) Field of Classification Search ............ 623/400; 528/25, 31, 32; 523/106, 113
See application file for complete search history.

(56) References Cited

U.S. PATENT DOCUMENTS

| | | |
|---|---|---|
| 4,153,641 A | 5/1979 | Deichert et al. |
| 4,189,546 A | 2/1980 | Deichert et al. |
| 4,254,248 A | 3/1981 | Friends et al. |
| 4,259,467 A | 3/1981 | Keogh et al. |
| 4,327,203 A | 4/1982 | Deichert et al. |
| 4,647,282 A | 3/1987 | Fedorov et al. |
| 5,077,335 A | 12/1991 | Schwabe et al. |
| 5,236,970 A | 8/1993 | Christ et al. |
| 5,371,147 A | 12/1994 | Spinelli et al. |
| 5,376,694 A | 12/1994 | Christ et al. |
| 5,444,106 A | 8/1995 | Zhou et al. |
| 5,451,617 A | 9/1995 | Lai et al. |
| 5,494,946 A | 2/1996 | Christ et al. |
| 5,512,609 A | 4/1996 | Yang |
| 5,623,029 A | 4/1997 | Yang |
| 5,661,195 A | 8/1997 | Christ et al. |
| 5,869,549 A | 2/1999 | Christ et al. |
| 5,945,498 A | 8/1999 | Hopken et al. |
| 5,962,548 A | 10/1999 | Vanderlaan et al. |
| 5,981,669 A | 11/1999 | Valint, Jr. et al. |
| 5,981,675 A | 11/1999 | Valint, Jr. et al. |
| 6,020,445 A | 2/2000 | Vanderlaan et al. |
| 6,066,172 A | 5/2000 | Huo et al. |
| 6,139,576 A | 10/2000 | Doyle et al. |
| 6,255,362 B1 | 7/2001 | Ito |
| 6,277,147 B1 | 8/2001 | Christ et al. |
| 6,361,561 B1 | 3/2002 | Huo et al. |
| 6,534,587 B1 * | 3/2003 | Tapsak et al. .......... 524/588 |

FOREIGN PATENT DOCUMENTS

| | | | |
|---|---|---|---|
| JP | 60-120755 A | * | 6/1985 |
| JP | 2000131655 A | | 5/2000 |
| JP | 2000131655 A | * | 5/2000 |

* cited by examiner

Primary Examiner—Marc S. Zimmer
(74) Attorney, Agent, or Firm—Fulwider Patton LLP

(57) ABSTRACT

High refractive index and optically clear copoly(carbosilane and siloxane) elastomers and ophthalmic lenses made therefrom are provided. The elastomers are comprised of copolymers having carbosilane repeat units and siloxane repeat units. The copolymers and ophthalmic lenses of the present invention have a high refractive index and excellent folding recoverability.

6 Claims, 2 Drawing Sheets

HIGH REFRACTIVE INDEX AND OPTICALLY CLEAR COPOLY (CARBOSILANE AND SILOXANE) ELASTOMERS

This application is a division of U.S. Ser. No. 10/308,803, filed Dec. 3, 2002.

FIELD OF THE INVENTION

The present invention is directed to high refractive index and optically clear elastomers, and ophthalmic lenses formed therefrom. More particularly, the invention relates to copoly(carbosilane and siloxane) elastomers.

BACKGROUND OF THE INVENTION

The physiology of the human eye includes an anterior chamber located between the cornea, or outer surface of the clear part of the eye, and the iris, the pigmented portion of the eye that is responsive to light, and a posterior chamber, filled with vitreous humor. A crystalline lens, which includes a lens matrix contained within a capsular bag, is located behind the iris and separates the iris from the posterior chamber. The crystalline lens is attached to the ciliary muscle by cord-like structures called zonules. Lining the rear of the posterior chamber is the retina, the light sensing organ of the eye, that is an extension of the optic nerve. In young, healthy eyes, contraction and relaxation of the ciliary muscle shapes the natural crystalline lens to the appropriate optical configuration for focusing light rays entering the eye on the retina.

As the natural crystalline lens ages, however, the structure of the lens matrix of the crystalline lens changes, becoming hazy and relatively inflexible. Eventually, the hazing of the lens matrix may progress to the point where the lens is considered cataractous, which may seriously occlude the amount of light passing through the crystalline lens and ultimately onto the retina. Fortunately, modern surgical techniques have been developed which allow removal of the cataractous lens matrix so that light may once again pass unimpeded onto the retina.

Presently, a cataractous crystalline lens matrix is removed from an eye using a procedure whereby the cataractous natural lens matrix is extracted from the capsular bag of the lens through an anterior capsulotomy. Typically, the cataractous lens matrix is removed from the capsular bag through the anterior capsulotomy using phaco-emulsification and aspiration. Alternatively, the cataractous lens matrix may be removed using several other well known techniques whereby the cataractous material is broken up and aspirated from the capsular bag. After extraction of the cataractous lens matrix, an intraocular lens may be implanted within the remaining capsular bag. However, while the procedure to remove the emulsified natural lens can be accomplished with about a three millimeter incision in the cornea, about at least a six millimeter incision is required to accommodate the full diameter of the intraocular lens to be implanted.

In order to reduce the size of the incision required for implantation of an intraocular lens, and thus limit the trauma to the eye, intraocular lenses made of relatively soft material that can be rolled, folded or otherwise deformed for insertion into the eye were developed, replacing conventional intraocular lenses made of relatively hard material, such as polymethylmethacrylate (PMMA). Soft intraocular lens must exhibit a number of important mechanical and physical properties to be suitable as an implant. For instance, soft intraocular lenses should have low glass transition temperatures so that they can be readily folded for implantation at room temperature. In addition, the thickness of the intraocular lens should be minimized in order to reduce the overall size of the folded or rolled lens. Thus, soft intraocular lenses should have a high refractive index so that the lenses will have the requisite refractory power at a minimal thickness. The lenses should also exhibit a high degree of softness to improve the foldability of the lenses, thereby reducing the size of the folded lens, while still retaining other mechanical properties, such as tensile strength and folding recoverability. Further, the lenses must be optically clear.

Prior art soft intraocular lenses made of silicone materials typically have very low glass transition temperatures (lower than −100° C.), permitting them to be readily folded or rolled at room temperature. However, other properties of silicone lenses could be improved in order to minimize the size of the folded lens. It would be desirable to provide a silicone material for use as an intraocular lens that has a high refractive index and softness to reduce the size of the folded lens. It would also be desirable to provide a silicone material that has other properties suitable for use as an intraocular lens such as high folding recoverability and optical clarity.

What has been needed and heretofore unavailable, is a silicone material having improved properties, including a high refractive index, softness, optical clarity and excellent folding recoverability, for use in intraocular lenses. The present invention satisfies these needs and others.

SUMMARY OF THE INVENTION

The present invention provides copoly(carbosilane and siloxane) elastomers useful in the fabrication of ophthalmic lenses, including intraocular lenses and other implantable ocular devices, such as intraocular contact lenses.

In one embodiment, the copoly(carbosilane and siloxane) elastomer comprises a copolymer having carbosilane repeat units and siloxane repeat units. Each carbosilane repeat unit has a carbon chain with 2 to 12 carbon atoms. Each siloxane repeat unit may be individually selected from the group comprising dimethylsiloxane and diphenylsiloxane.

The copolymers of the present invention also have terminal alkenyl groups in one embodiment. More particularly, each terminal alkenyl group may be selected from the group consisting of vinyl, allyl, vinylphenyl, allylphenyl, vinylbenzyl and allylbenzyl.

In another embodiment, the copolymer has the structure (I):

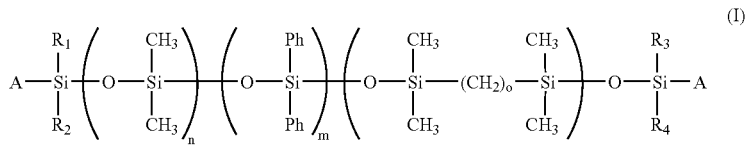

wherein A is an alkynyl; R1, R2, R3, and R4 are each a hydrocarbon group; Ph is a phenyl; n is an integer from 10 to 500; m is an integer from 5 to 100; o is an integer from 2 to 12; and p is an integer from 2 to 50.

In other embodiments, additional materials are also included in the elastomer to achieve desired properties. In one embodiment, the elastomer includes a platinum catalyst. In another embodiment, the elastomer includes a crosslinking agent, such as an organohydrosilane having multiple hydride groups or containing multiple hydride group polymers. More particularly, the crosslinking agent is a hydrodimethyl-terminated silazane in one embodiment. In yet another embodiment, a filler that is hexamethyldisilazane-treated silica and silicone resin material is added to the elastomer. Further, an ultraviolet (UV) light absorbing compound, such as allyl or methallyl functionalized benzotriazoles and benzophenones, may also be included in the elastomer.

The elastomers of the present invention have a high refractive index, at least about 1.43 in one embodiment. The elastomers also have excellent folding recoverability.

In one embodiment, an ophthalmic lens is formed from the copoly(carbosilane and siloxane) elastomers. In particular, the ophthalmic lens may be an intraocular lens. The ophthalmic lens may also be an intraocular contact lens or other implantable ocular device.

The elastomers of the present invention are particularly suited for use in ophthalmic lenses due to their high refractive index and optical clarity. The elastomers are also soft materials with excellent folding recoverability, permitting lenses formed therefrom to be folded or rolled to a minimal size for insertion. The elastomers also have high strength and flexibility and are photostable.

Other features and advantages of the invention will become apparent from the following detailed description, taken in conjunction with the drawings, which illustrate, by way of example, various embodiments, principles and features of the invention.

DETAILED DESCRIPTION OF THE PREFERRED EMBODIMENTS

Figure 1A:
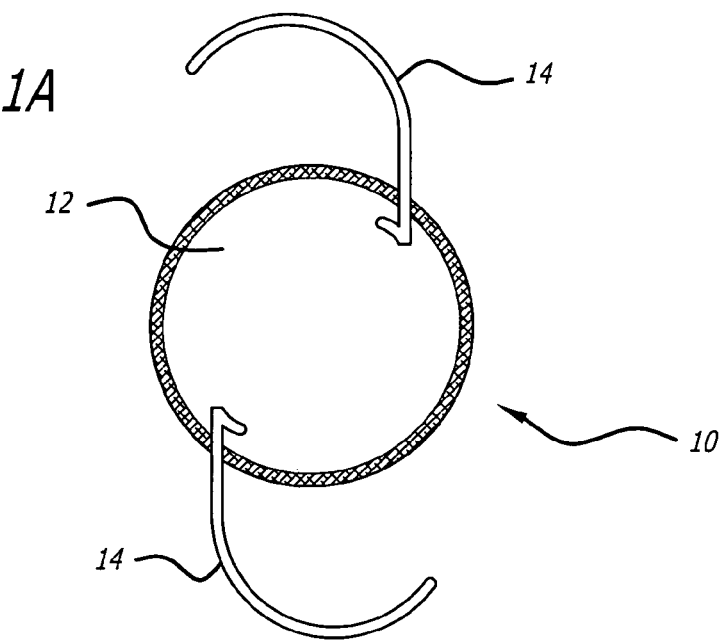
FIG. 1A is a top view of an embodiment of an intraocular lens of the present invention, having an optic and a pair of haptics.

The present invention relates to elastomers having a high refractive index and optical clarity, and ophthalmic lenses made therefrom. Specifically, the invention relates to copoly(carbosilane and siloxane) elastomers having a high refractive index and optical clarity that are suitable for implantation within an eye of a patient.

The elastomers of the present invention include a copolymer having carbosilane repeat units and siloxane repeat units. In one embodiment, each carbosilane repeat unit has a carbon chain with 2 to 12 carbon atoms. Generally, about 2 to 50 carbosilane repeat units are present in a chain of the copolymer, although more carbosilane repeat units, such as 50 or more, may be present. The carbosilane repeat units generally comprise about 2% to 5% by weight of the copolymer.

The copolymers of the present invention also include siloxane repeat units. The siloxane repeat units have up to two carbon groups attached to each silicon atom in one embodiment. These carbon groups may be methyl or phenyl groups. In particular, suitable siloxane repeat units include, but are not limited to, dimethylsiloxane, methylphenylsiloxane, and diphenylsiloxane. Generally, about 10 to 500 dimethylsiloxane repeat units and about 5 to 500 diphenylsiloxane repeat units are present in a chain of the copolymer. The dimethylsiloxane and diphenylsiloxane repeat units generally comprise about 50% to 98% by weight of the copolymer.

In one embodiment, the copoly(carbosilane and siloxane) is a random copolymer having the structure (I):

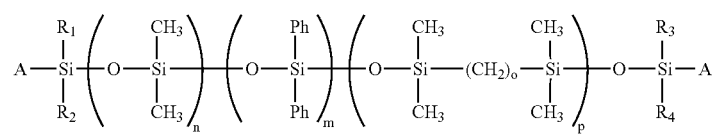

wherein A is an alkenyl; R1, R2, R3, and R4 are each a hydrocarbon group; Ph is a phenyl; n is an integer from 10 to 500; m is an integer from 5 to 100; o is an integer from 2 to 12; and p is an integer from 2 to 50.

Suitable terminal alkenyl groups (A) include, but are not limited to, vinyl, allyl, vinylphenyl, allylphenyl, vinylbenzyl and allylbenzyl. The suitable hydrocarbon groups for R1, R2, R3, and R4 include but are not limited to allyl or aryl groups, such as ethyl, methyl, propyl, butyl and phenyl.

The elastomer may include a platinum catalyst, such as a platinum divinyl complex having 2–3% platinum in xylene, that is added to catalyze the curing of the elastomer, as is well known in the art. Additionally, the elastomer may include a crosslinking agent. Suitable crosslinking agents include organohydrosilanes having multiple hydride groups or containing multiple hydride group polymers. In one embodiment, a hydrodimethyl-terminated silicone is used as the crosslinking agent. be present. The carbosilane repeat units generally comprise about 2% to 5% by weight of the copolymer.

The copolymers of the present invention also include siloxane repeat units. The siloxane repeat units have up to two carbon groups attached to each silicon atom in one embodiment. These carbon groups may be methyl or phenyl groups. In particular, suitable siloxane repeat units include, but are not limited to, dimethylsiloxane, methylphenylsiloxane, and diphenylsiloxane. Generally, about 10 to 500 dimethylsiloxane repeat units and about 5 to 500 diphenylsiloxane repeat units are present in a chain of the copolymer. The dimethylsiloxane and diphenylsiloxane repeat units generally comprise about 50% to 98% by weight of the copolymer.

In one embodiment, the copoly(carbosilane and siloxane) is a random copolymer having the structure (I):

silica and silicone resin material. The filler may be added in amount of about 8–25 parts filler to 75–92 parts copolymer.

The elastomers of the present invention may also include an ultraviolet (UV) light absorbing compound, such as allyl or methallyl functionalized benzotriazoles or benzophenones, for protection against excessive UV radiation. The UV absorbing component may be pre-linked to the crosslinking agent or mixed in separately with the copoly (carbosilane and siloxane).

The copolymer having carbosilane and siloxane repeat units may be prepared, for example, by the reaction of octamethylcyclotetrasiloxane and octaphenylcyclotetrasiloxane with vinyl-terminated oligo(carbosilane and siloxane) in the presence of an N-catalyst, such as tetramethylammonium hydroxide or tetraethylammonium hydroxide, at high temperature. The vinyl-terminated oligo(carbosilane and siloxane) may have a molecular weight of about 400 to 4000 and from 2 to 50 repeat units of carbosilane. The viscosity of the base copolymer used in the preparation of the final elastomer can range from about 500 cps to 50,000 cps, and preferrably 2000 cps to 10000 cps. The base copolymer may then be cured to form the elastomer of the present invention by methods well known in the art.

The resulting elastomers are soft, biocompatible and optically clear. The elastomers have a durometer Shore A hardness of at least 15. Further, they have an elongation of at least 100 percent, and a tensile strength of at least about 100 psi, and preferably about 180 to 260 psi. The elastomers of the present invention have a high refractive index, between about 1.43 to 1.55 (at 20° C.) in one embodiment, and more particularly at least about 1.46 in another embodiment.

The elastomers are particularly useful in the fabrication of ophthalmic lenses and other implantable ocular devices,

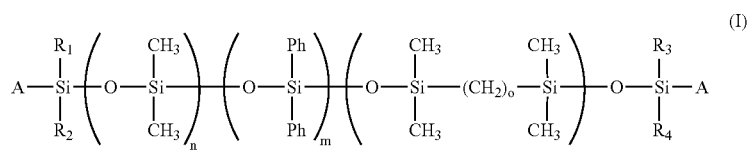

(I)

wherein A is an alkynyl; $R_1$, $R_2$, $R_3$, and $R_4$ are each a hydrocarbon group; Ph is a phenyl; n is an integer from 10 to 500; m is an integer from 5 to 100; o is an integer from 2 to 12; and p is an integer from 2 to 50.

Suitable terminal alkynyl groups (A) include, but are not limited to, vinyl, allyl, vinylphenyl, allylphenyl, vinylbenzyl and allylbenzyl. The suitable hydrocarbon groups for $R_1$, $R_2$, $R_3$, and $R_4$ include but are not limited to allyl or aryl groups, such as ethyl, methyl, propyl, butyl and phenyl.

The elastomer may include a platinum catalyst, such as a platinum divinyl complex having 2–3% platinum in xylene, that is added to catalyze the curing of the elastomer, as is well known in the art. Additionally, the elastomer may include a crosslinking agent. Suitable crosslinking agents include organohydrosilanes having multiple hydride groups or containing multiple hydride group polymers. In one embodiment, a hydrodimethyl-terminated silicone is used as the crosslinking agent.

A filler may also be included in the elastomer to reinforce the mechanical properties of the crosslinked elastomer. In one embodiment, the filler is hexamethyldisilazane-treated including intraocular lenses and intraocular contact lenses. The elastomers may be advantageously used for the lens body of the ophthalmic lens, or more particularly the optic of an intraocular lens. The elastomers are soft, biocompatible, and optically clear and have a high refractive index and high strength. They are capable of being deformed for insertion through a small incision in the cornea without breakage and have excellent folding recoverability. The elastomers are also photostable.

The ophthalmic lens bodies may be molded at temperatures of 120° C. to 200° C.; preferably the molding temperature is in the range of 145° C. to 160° C. In yet another embodiment, the lens mold may be shaped so as to produce a lens having suitable curves and geometry such that the molded lens requires little or no additional forming to provide a finished lens.

Figure 1B:
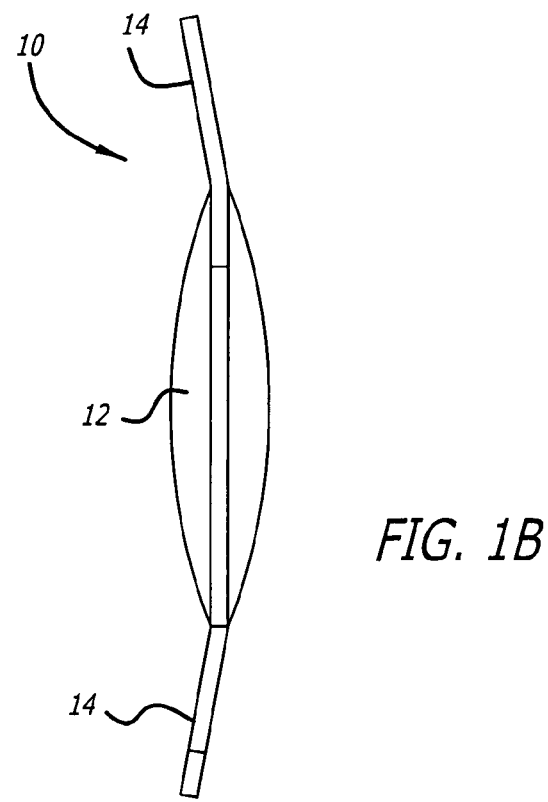
FIG. 1B is a side view of the embodiment of FIG. 1A.

FIG. 1A depicts an embodiment of an intraocular lens 10 of the present invention. The intraocular lens 10 has an optic 12 formed from a elastomer of the present invention and flexible haptics 14 for positioning the intraocular lens 10 in the eye. The intraocular lens 10 may have one or more haptics, although in this embodiment, two haptics 14 are shown. Also, in this embodiment, the intraocular lens 10 is shown as a multi-piece lens wherein the optic 12 and the haptics 14 are formed from different materials and the haptics 14 are attached to the optic 12 by conventional methods. The haptics 14 may be, for example, a filament of PMMA, polyimide, Kynar® or polypropylene formed by extrusion. As one skilled in the art will appreciate, the intraocular lens may alternatively be a one-piece design wherein the optic and haptics are formed from a single piece of the elastomer of the present invention. FIG. 1B depicts a side view of the intraocular lens 10 of FIG. 1A, further showing the optic 12 and haptics 14.

Figure 2B:
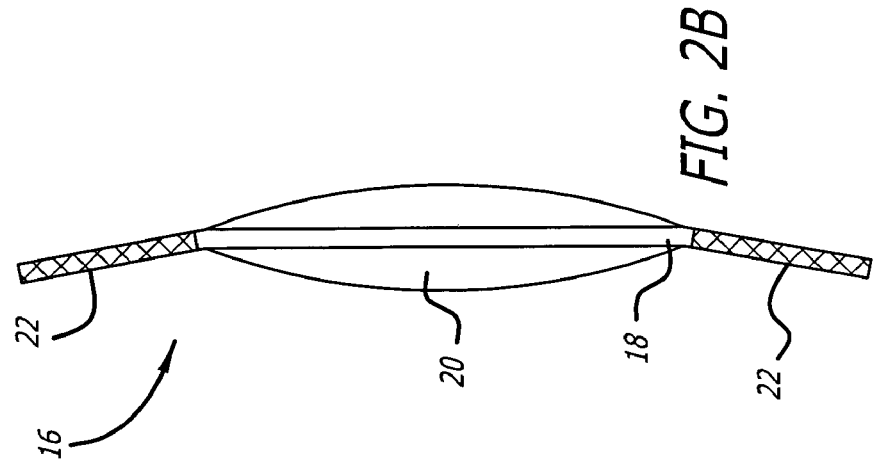
FIG. 2B is a side view of the embodiment of FIG. 2A.
Figure 2A:
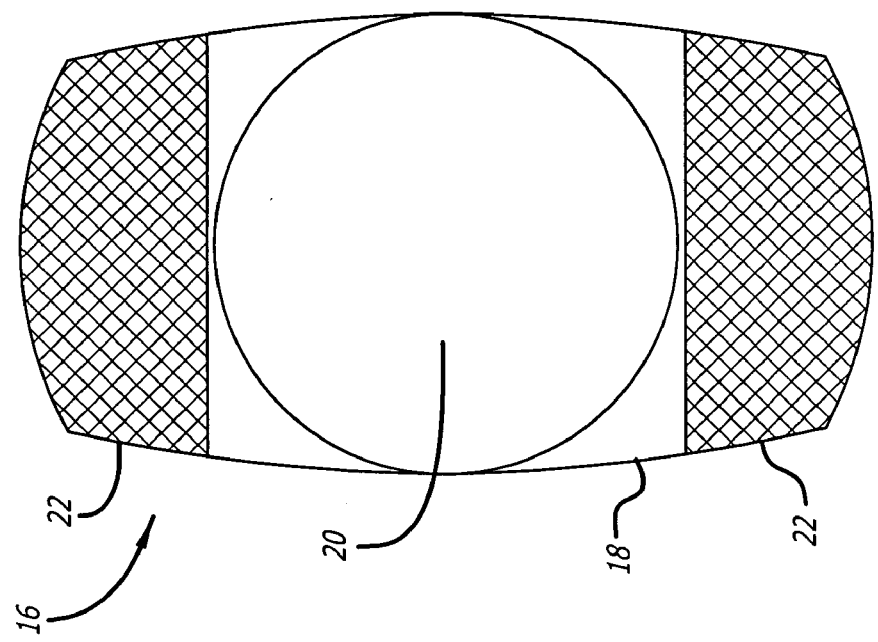
FIG. 2A is a top view of an embodiment of an intraocular lens of the present invention having an optic and a pair of plate-type haptics.

FIG. 2A depicts another embodiment of an intraocular lens of the present invention. In FIG. 2A, a plate-type haptics lens 16 having a lens body 18 is shown. As seen from the illustration in FIG. 3A, the lens body 18 has a generally rectangular shape and includes a central optic zone or optic 20 formed from a elastomer of the present invention and plate-type haptics 22 extending from diametrically opposite edges of the optic 20. FIG. 2B depicts a side-view of the plate-type haptics lens 16 shown in FIG. 2A.

In addition, the elastomers of the present invention can be used to produce other transparent objects requiring a high refractive index and an optically clear, soft material.

The invention will now be further illustrated by the following examples which are intended to be illustrative and non-limiting.

EXAMPLE 1

This example illustrates the preparation of oligo(carbosilane and siloxane) (A) which is used in the preparation of the copoly(carbosilane and siloxane) elastomer. In a 250 ml three-necked round bottom flask, 150 grams of 1,3-divinyltetramethyldisiloxane and 13 milligrams of platinum catalyst were stirred and heated to 100° C. Over a period of 25 minutes, 25 grams of tetramethyldisiloxane were added dropwise to the flask. The mixture was stirred at 100° C. for an additional hour. Excess 1,3-divinyltetramethyldisiloxane was removed under vacuum conditions until no further low boiling point material remained, leaving behind a yellow, slightly viscous material. GPC analysis showed that this material had an average molecular weight of about 500. $^1$H NMR spectra showed that the material was oligo(carbosilane and siloxane).

EXAMPLE 2

A higher molecular weight oligo(carbosilane and siloxane) (B) was prepared from the oligo(carbosilane and siloxane) (A) of Example 1 as follows. In a 250 ml three-necked round bottom flask, 15 grams of tetramethyldisiloxane and 13 milligrams of platinum catalyst were stirred and heated to 80° C. Over a period of 15 minutes, 15 grams of oligo (carbosilane and siloxane) (A) were added dropwise to the flask. The mixture was stirred at 100° C. for an additional hour. Excess tetramethyldisiloxane was removed under vacuum conditions until no further low boiling point material remained. The mixture was then cooled to room temperature.

Next, 50 grams of 1,3-divinyltetramethyldisiloxane and 13 milligrams of catalyst are added to a second 250 ml three-necked round bottom flask and stirred and heated to 100° C. Over a period of 15 minutes, the material from the first flask was added dropwise to the second flask. The mixture was stirred at 100° C. for an additional hour. Low boiling point material was removed under high vacuum, leaving behind a yellow, high viscosity oligomer (B). GPC analysis showed that this material had an average molecular weight of about 1000. $^1$H NMR spectra showed that the material was oligo(carbosilane and siloxane).

EXAMPLE 3

Examples 3 through 7 illustrate the preparation of copoly (carbosilane and siloxane) from oligo(carbosilane and siloxane) A and B in accordance with principles of the present invention.

In a 500 ml three-necked round bottom flask, 44.6 grams of octaphenylcyclotetrasiloxane, 93.5 grams of octamethylcyclotetrasiloxane, 5.1 grams of vinyldimethylsiloxy-terminated oligo(carbosilane and siloxane) (B) and 0.14 grams of N-catalyst were mixed. The mixture was stirred and heated to 100° to 120° C. for 2 to 4 hours until the octaphenylcyclotetrasiloxane had completely dissolved and the mixture turned into a viscous brown solution. The mixture was then cooled to room temperature and 150 ml of methylene chloride was added and stirred into the mixture. Next, 75 ml of methyl alcohol and 100 ml of distilled water were added and the mixture was stirred again at room temperature for 15 minutes. The organic layer was separated and another 75 ml of methyl alcohol and 100 ml of distilled water were added to the separated organic layer. The organic layer was separated again and dried over magnesium sulfate. After filtering, the solvent was then removed under vacuum. The resulting material was a colorless copoly(carbosilane and siloxane) with a viscosity of 4400 cps and a refractive index of 1.465.

EXAMPLE 4

In a 500 ml three-necked round bottom flask, 41.0 grams of octaphenylcyclotetrasiloxane, 99.0 grams of octamethylcyclotetrasiloxane, 6.1 grams of vinyldimethylsiloxy-terminated oligo(carbosilane and siloxane) (B) and 0.14 grams of N-catalyst were mixed. The mixture was stirred and heated to 100° to 120° C. for 2 to 4 hours until the octaphenylcyclotetrasiloxane had completely dissolved and the mixture turned into a viscous brown solution. The mixture was then cooled to room temperature and 150 ml of methylene chloride was added and stirred into the mixture. Next, 75 ml of methyl alcohol and 100 ml of distilled water were added and the mixture was stirred again at room temperature for 15 minutes. The organic layer was separated and another 75 ml of methyl alcohol and 100 ml of distilled water were added to the separated organic layer. The organic layer was separated again and dried over magnesium sulfate. After filtering, the solvent was then removed under vacuum. The resulting material was a colorless copoly(carbosilane and siloxane) with a viscosity of 4200 cps and a refractive index of 1.462.

EXAMPLE 5

In a 500 ml three-necked round bottom flask, 44.6 grams of octaphenylcyclotetrasiloxane, 93.5 grams of octamethylcyclotetrasiloxane, 3.1 grams of vinyldimethylsiloxy-terminated oligo(carbosilane and siloxane) (A) and 0.14 grams of N-catalyst were mixed. The mixture was stirred and heated to 100° to 120° C. for 2 to 4 hours until the octaphenylcyclotetrasiloxane had completely dissolved and the mixture turned into a viscous brown solution. The mixture was then cooled to room temperature and 150 ml of methylene chloride was added and stirred into the mixture. Next, 75 ml of methyl alcohol and 100 ml of distilled water were added and the mixture was stirred again at room temperature for 15 minutes. The organic layer was separated and another 75 ml of methyl alcohol and 100 ml of distilled water were added to the separated organic layer. The organic layer was separated again and dried over magnesium sulfate. After filtering, the solvent was then removed under vacuum. The resulting material was a colorless copoly(carbosilane and siloxane) with a viscosity of 4600 cps and a refractive index of 1.466.

EXAMPLE 6

In a 500 ml three-necked round bottom flask, 40.0 grams of octaphenylcyclotetrasiloxane, 93.5 grams of octamethylcyclotetrasiloxane, 3.1 grams of vinyldimethylsiloxy-terminated oligo(carbosilane and siloxane) (A) and 0.14 grams of N-catalyst were mixed. The mixture was stirred and heated to 100° to 120° C. for 2 to 4 hours until the octaphenylcyclotetrasiloxane had completely dissolved and the mixture turned into a viscous brown solution. The mixture was then cooled to room temperature and 150 ml of methylene chloride was added and stirred into the mixture. Next, 75 ml of methyl alcohol and 100 ml of distilled water were added and the mixture was stirred again at room temperature for 15 minutes. The organic layer was separated and another 75 ml of methyl alcohol and 100 ml of distilled water were added to the separated organic layer. The organic layer was separated again and dried over magnesium sulfate. After filtering, the solvent was then removed under vacuum. The resulting material was a colorless copoly(carbosilane and siloxane) with a viscosity of 4150 cps and a refractive index of 1.462.

EXAMPLE 7

In a 500 ml three-necked round bottom flask, 41.0 grams of octaphenylcyclotetrasiloxane, 99.0 grams of octamethylcyclotetrasiloxane, 3.6 grams of vinyldimethylsiloxy-terminated oligo(carbosilane and siloxane) (A) and 0.17 grams of N-catalyst were mixed. The mixture was stirred and heated to 100° to 120° C. for 2 to 4 hours until the octaphenylcyclotetrasiloxane had completely dissolved and the mixture turned into a viscous brown solution. The mixture was then cooled to room temperature and 150 ml of methylene chloride was added and stirred into the mixture. Next, 75 ml of methyl alcohol and 100 ml of distilled water were added and the mixture was stirred again at room temperature for 15 minutes. The organic layer was separated and another 75 ml of methyl alcohol and 100 ml of distilled water were added to the separated organic layer. The organic layer was separated again and dried over magnesium sulfate. After filtering, the solvent was then removed under vacuum. The resulting material was a colorless copoly(carbosilane and siloxane) with a viscosity of 8650 cps and a refractive index of 1.461.

TABLE 1 summarizes the compositions and properties of the copolymers of Examples 3 through 7.

TABLE 1

| | Example #: | | | | |
|---|---|---|---|---|---|
| | 3 | 4 | 5 | 6 | 7 |
| Composition (g) | | | | | |
| $D_4Ph$ | 44.6 | 41.0 | 44.6 | 40.0 | 41.0 |
| $D_4$ | 93.5 | 99.0 | 93.5 | 93.5 | 99.0 |
| OCS | 5.1(B) | 6.1(B) | 3.1(A) | 3.1(A) | 3.6(A) |
| N-catalyst | 0.14 | 0.14 | 0.14 | 0.14 | 0.17 |
| Properties | | | | | |
| Viscosity (cps) | 4400 | 4200 | 4600 | 4150 | 8650 |
| Refractive Index | 1.465 | 1.462 | 1.466 | 1.462 | 1.46 |

$D_4Ph$—octaphenylcyclotetrasiloxane
$D_4$—octamethylcyclotetrasiloxane
OCS—oligo(carbosilane and siloxane)

EXAMPLE 8

The remaining examples illustrate the preparation of various embodiments of the elastomer of the present invention from the exemplary copolymers prepared in Examples 3 through 7.

In a 500 ml glass flask, 80.0 grams of the copolymer of Example 3 was mixed with 24.0 grams of hexamethyldisilazane-treated silica. The mixture was mechanically stirred and heated to 120° C. for 2 to 5 hours. Then, the mixture was cooled to room temperature and 4.0 grams of hydrodimethyl-terminated silicone crosslinking agent, 1.0 grams of tris(vinyldimethylsiloxysilane), 104.0 milligrams of tetravinyltetramethylcyclotetrasiloxane, and 26.0 milligrams of platinum divinyl complex (2–3% platinum concentration in xylene) were added and mixed until the mixture turned clear. The mixture was degassed for about 20 to 50 minutes to remove all air bubbles in the mixture. The mixture was then transferred into a sheet casting fixture and cast at 150° C. for 1.5 hours. After cooling to room temperature, the sheet was removed and cut into the desired shape. The final product had an elongation of 195% and a tensile strength of 260 psi.

EXAMPLE 9

In a 500 ml glass flask, 80.0 grams of the copolymer of Example 4 was mixed with 16.0 grams of hexamethyldisilazane-treated silica. The mixture was stirred and heated to 120° C. for 2 to 5 hours. Then, the mixture was cooled to room temperature and 2.0 gram of hydrodimethyl-terminated silicone crosslinking agent, 104.0 milligrams of tetravinyltetramethylcyclotetrasiloxane, and 13.0 milligrams of platinum divinyl complex (2–3% platinum concentration in xylene) were added and mixed until the mixture turned clear. The mixture was degassed for about 20 to 50 minutes to remove all air bubbles in the mixture. The mixture was then transferred into a sheet casting fixture and cast at 150° C. for 1.5 hours. After cooling to room temperature, the sheet was removed and cut into the desired shape. The final product had an elongation of 150% and a tensile strength of 210 psi.

EXAMPLE 10

In a 500 ml glass flask, 80.0 grams of the copolymer of Example 5 was mixed with 22.5 grams of hexamethyldisilazane-treated silica. The mixture was stirred and heated to 120° C. for 2 to 5 hours. Then, the mixture was cooled to room temperature and 4.0 grams of hydrodimethyl-terminated silicone crosslinking agent, 1.0 grams of tris(vinyldimethylsiloxysilane), 104.0 milligrams of tetravinyltetramethylcyclotetrasiloxane, and 26.0 milligrams of platinum divinyl complex (2–3% platinum concentration in xylene) were added and mixed until the mixture turned clear. The mixture was degassed for about 20 to 50 minutes to remove all air bubbles in the mixture. The mixture was then transferred into a sheet casting fixture and cast at 150° C. for 1.5 hours. After cooling to room temperature, the sheet was removed and cut into the desired shape. The final product had an elongation of 200% and a tensile strength of 210 psi.

EXAMPLE 11

In a 500 ml glass flask, 80.0 grams of the copolymer of Example 6 was mixed with 24.0 grams of hexamethyldisilazane-treated silica. The mixture was stirred and heated to 120° C. for 2 to 5 hours. Then, the mixture was cooled to room temperature and 4.0 grams of hydrodimethyl-terminated silicone crosslinking agent, 104.0 milligrams of tetravinyltetramethylcyclotetrasiloxane, and 26.0 milligrams of platinum divinyl complex (2–3% platinum concentration in xylene) were added and mixed until the mixture turned clear. The mixture was degassed for about 20 to 50 minutes to remove all air bubbles in the mixture. The mixture was then transferred into a sheet casting fixture and cast at 150° C. for 1.5 hours. After cooling to room temperature, the sheet was removed and cut into the desired shape. The final product had an elongation of 200% and a tensile strength of 230 psi.

EXAMPLE 12

In a 500 ml glass flask, 80.0 grams of the copolymer of Example 7 was mixed with 8.5 grams of hexamethyldisilazane-treated silica. The mixture was stirred and heated to 120° C. for 2 to 5 hours. Then, the mixture was cooled to room temperature and 2.4 grams of hydrodimethyl-terminated silicone crosslinking agent, 104.0 milligrams of tetravinyltetramethylcyclotetrasiloxane, and 26.0 milligrams of platinum divinyl complex (2–3% platinum concentration in xylene) were added and mixed until the mixture turned clear. The mixture was degassed for about 20 to 50 minutes to remove all air bubbles in the mixture. The mixture was then transferred into a sheet casting fixture and cast at 150° C. for 1.5 hours. After cooling to room temperature, the sheet was removed and cut into the desired shape. The final product had an elongation of 180% and a tensile strength of 180 psi.

Table 2 summarizes the elastomer compositions and properties of Examples 8 through 12.

TABLE 2

| | Example #: | | | | |
|---|---|---|---|---|---|
| | 8 | 9 | 10 | 11 | 12 |
| Composition (g) | | | | | |
| CPCS | 80.0 | 80.0 | 80.0 | 80.0 | 80.0 |
| Silica | 24.0 | 16.0 | 22.5 | 22.5 | 8.5 |
| Crosslinker | 4.0 | 2.0 | 4.0 | 2.4 | 2.4 |
| TVDMS | 1.0 | | 1.0 | | |
| TVTMCTS | 0.104 | 0.104 | 0.104 | 0.104 | 0.104 |
| Platinum Catalyst | 0.026 | 0.026 | 0.026 | 0.026 | 0.026 |
| Properties | | | | | |
| Elongation (%) | 195 | 150 | 200 | 200 | 180 |
| Tensile Strength (psi) | 260 | 210 | 210 | 230 | 280 |

CPCS—copoly(carbosilane and siloxane)
Silica—hexamethyldisilazane treated silica
Crosslinker—hydrodimethylsiloxane
TVDMS—tris(vinyldimethylsiloxysilane)
TVTMCTS—tetravinyltetramethylcyclotetrasiloxane While several specific embodiments of the invention have been illustrated and described, it will be apparent that various modifications can be made without departing from the spirit and scope of the invention. Accordingly, it is not intended that the invention be limited, except as by the appended claims.

What is claimed is:

1. A copoly (carbosilane and siloxane) elastomer having optical clarity comprising:

a crosslinkable copolymer consisting of carbosilane repeat units and siloxane repeat units, the carbosilane repeat units each having a carbon chain with 2 to 12 carbon atoms and the siloxane repeat units each being independently selected from the group consisting of dimethylsiloxane and diphenylsiloxane; and a crosslinking agent;

wherein the elastomer has a refractive index of at least 1.43.

2. The elastomer of claim 1, wherein the copolymer has the structure:

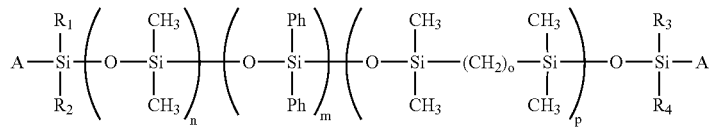

wherein

A is an alkenyl;

$R_1$, $R_2$, $R_3$, and $R_4$ are each a hydrocarbon group;

Ph is a phenyl;

n is an integer from 10 to 500;

m is an integer from 5 to 100;

o is an integer from 2 to 12; and p is an integer from 2 to 50.

3. The elastomer of claim 1 further comprising a platinum catalyst.

4. The elastomer of claim 1, wherein the crosslinking agent is a hydrodimethyl-terminated silicone.

5. The elastomer of claim 1 further comprising a filler that is hexamethyldisilazane-treated silica and silicone resin material.

6. The elastomer of claim 1 further comprising a UV absorbing compound selected from the group consisting of allyl or methallyl functionalized benzotriazoles or benzophenones.

* * * * *

UNITED STATES PATENT AND TRADEMARK OFFICE
CERTIFICATE OF CORRECTION

| | | |
|---|---|---|
| PATENT NO. | : 7,071,279 B2 | Page 1 of 1 |
| APPLICATION NO. | : 10/826498 | |
| DATED | : July 4, 2006 | |
| INVENTOR(S) | : Xiugao Liao | |

It is certified that error appears in the above-identified patent and that said Letters Patent is hereby corrected as shown below:

Column 3,
Line 14, delete "R1, R2, R3, and R4" and insert --$R_1$, $R_2$, $R_3$, and $R_4$--.

Column 5,
Line 1, delete "R1, R2, R3, and R4" and insert --$R_1$, $R_2$, $R_3$, and $R_4$--.
Lines 7-8, delete "R1, R2, R3, and R4" and insert --$R_1$, $R_2$, $R_3$, and $R_4$--.
Line 18, delete "be present. The carbosilane repeat".
Lines 19 through 64, delete.

Signed and Sealed this

Twenty-fourth Day of October, 2006

JON W. DUDAS
*Director of the United States Patent and Trademark Office*